United States Patent [19]

Kolner

[11] Patent Number: 5,324,412

[45] Date of Patent: Jun. 28, 1994

[54] ELECTROPHORESIS PLATES WITH GROOVES

[75] Inventor: Douglas E. Kolner, Madison, Wis.

[73] Assignee: Wisconsin Alumni Research Foundation, Madison, Wis.

[21] Appl. No.: 908,688

[22] Filed: Jul. 2, 1992

[51] Int. Cl.⁵ .................... G01N 27/26; G01N 27/447
[52] U.S. Cl. ............................ 204/299 R; 204/182.8
[58] Field of Search ..................... 204/299 R, 182.8

[56] References Cited

U.S. PATENT DOCUMENTS

| | | | |
|---|---|---|---|
| 3,879,280 | 4/1975 | Peterson et al. | 204/299 R |
| 4,035,377 | 7/1977 | Detroy | 204/299 R |
| 4,715,942 | 12/1987 | Tezuka et al. | 204/299 R |
| 4,909,918 | 3/1990 | Bambeck et al. | 204/299 R |
| 4,915,811 | 4/1990 | Yamamoto et al. | 204/299 R |
| 5,073,246 | 12/1991 | Chu et al. | 204/299 R |

Primary Examiner—John Niebling
Assistant Examiner—John S. Starsiak, Jr.
Attorney, Agent, or Firm—Quarles & Brady

[57] ABSTRACT

An electrophoresis apparatus is disclosed. A first vertical support plate is attached to a base and contains grooves at its upper end. A second vertical support plate is spaced from the first plate by a spacer. The apparatus contains means for passing an electric current through a polymerized gel that may be formed in the space between the first vertical plate and the second vertical plate.

3 Claims, 2 Drawing Sheets

ELECTROPHORESIS PLATES WITH GROOVES

REFERENCE TO GOVERNMENT SUPPORT

This invention was made with U.S. government support awarded by the National Institute of Health (NIH), Grant #8 RO1 HG00321-02. The U.S. Government has certain rights in this invention.

FIELD OF THE INVENTION

The invention generally relates to devices for the electrophoretic separation of molecules. Specifically, the present invention relates to grooved plates used in a device for vertical electrophoresis.

BACKGROUND OF THE INVENTION

Electrophoresis is the process of separating molecules on the basis of the molecule's migration in an electric field. In an electric field, a molecule will migrate towards the pole that carries a charge opposite to the charge carried by the molecule. The charge carried by a molecule depends upon the pH of the medium in which the molecule is migrating. A common electrophoretic procedure is to set up solutions at different pH at each end of an electric field. At a certain pH, the isoelectric point of a molecule is obtained and the molecule carries no net charge. Therefore, as the molecule crosses the pH gradient, the molecule reaches an isoelectric point and is immobile in the electric field. Therefore, this electrophoresis separates molecules according to their different isoelectric points.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by both molecular size and isoelectric point.

Electrophoresis in a polymeric gel can also be used to separate molecules only by molecular size. Some groups of molecules, such as RNA and DNA molecules, all have the same isoelectric point. These groups of molecules will always migrate through an electric field across a polymeric gel on the basis of molecular size. Molecules with different isoelectric points, such as proteins, can be denatured in a solution of detergent, such as sodium dodecyl sulfate (SDS). The SDS-covered proteins will have similar isoelectric points and will migrate through the gel on the basis of molecular size. The separation of DNA molecules on the basis of their molecular size is an important step in determining the nucleotide sequence of a DNA molecule.

A polymeric gel electrophoresis system is typically set up in the following way: A gel-forming solution is allowed to polymerize between two glass plates that are held apart on two sides by spacers. These spacers determine the thickness of the gel. Typically, sample wells are formed by inserting a comb-shaped mold into the liquid between the glass plates at one end and allowing the liquid to polymerize around the mold. Alternatively, the gel may be cast with a flat top and a pointed comb inserted between the plates so that the points are slightly imbedded in the gel. Small, fluid-tight areas between the points can be filled with a sample.

The top and bottom of the polymerized gel are placed in electrical contact with two buffer reservoirs. Macromolecule samples are loaded into the sample wells. A sample-loading implement, such as a pipette, is inserted between the two glass plates and the sample is injected into the well. To prevent sample mixing, it is advantageous to inject the sample as close to the gel as possible. It is difficult to place the tip of the pipette or loading implement close to the gel because the pipette tip is often wider than the gel.

An electric field is set up across the gel, and the molecules begin to move into the gel and separate according to their size. The size-sorted molecules can be visualized in several ways. After electrophoresis, the gels can be bathed in a nucleotide-specific or protein-specific stain which renders the groups of size-sorted molecules visible to the eye. For greater resolution, the molecules can be radioactively labelled and the gel exposed to X-ray film. The developed X-ray film will indicate the migration positions of the labelled molecules.

Both vertical and horizontal assemblies are routinely used in gel electrophoresis. In a vertical apparatus, the sample wells are formed in the same plane as the gel and are loaded vertically. The wells can be as deep and wide as needed, but the thickness of the well is limited by the thickness of the gel.

Ultra-thin electrophoretic gels (less than 0.2 mm) are useful because they may be electrophoresed at a higher voltage than thicker gels. Therefore, the electrophoretic run is faster. Another advantage of ultra-thin gels is higher resolution because less sample is needed. Because of their thinness, the ultra-thin gels are fixed for autoradiography quickly and easily.

The problem of sample loading is especially burdensome with ultra-thin gel electrophoresis. The dimensions of the sample well are usually determined by the thickness of the gel. Therefore, ultra-thin gels have ultra-thin sample wells. Practically, it is difficult to load gels less than 1 mm thickness with a conventional pipette or less than 0.2 mm in thickness with a capillary tube. Sample loading can be accomplished using very thin, flat pipette tips or pulled glass capillaries to deposit samples into the wells. However, viscous samples are difficult to pipette with these loading devices because the devices can clog and break readily.

What is needed in the art of electrophoresis is a device that enables easier loading of ultra-thin electrophoretic gels.

SUMMARY OF THE INVENTION

The present invention is an electrophoresis apparatus. Two vertical support plates are spaced from each other by a spacer and attached to a base. The first vertical support plate contains grooves at its upper end. The apparatus contains a means for passing an electric current through a polymerized gel that may be formed in the space between the first and the second vertical plates.

An object of the present invention is to provide an electrophoresis apparatus that enables one to more easily load samples into sample wells formed at the upper end of the gel.

Another object of the present invention is to provide an electrophoresis apparatus that provides easier loading of samples into sample wells in an ultra-thin gel.

It is an advantage of the present invention that conventional pipette tips may be used to load an ultrathin vertical electrophoresis gel.

It is another advantage of the present invention that the sample may be loaded more closely to the gel surface.

Other objects, advantages and features of the present invention will become apparent upon examination of the specification, drawings and claims.

BRIEF DESCRIPTION OF THE PREFERRED EMBODIMENT

The present invention provides an electrophoretic apparatus comprising a plate with grooves ground into the gel-loading end of the plate. These grooves are vertically oriented and aligned with sample-holding wells in the gel and allow one to more easily inject sample with a sample-loading implement, such as a pipette or a capillary tube, into the well. This arrangement of grooves and gel will allow the gel to be more easily loaded.

Figure 1:
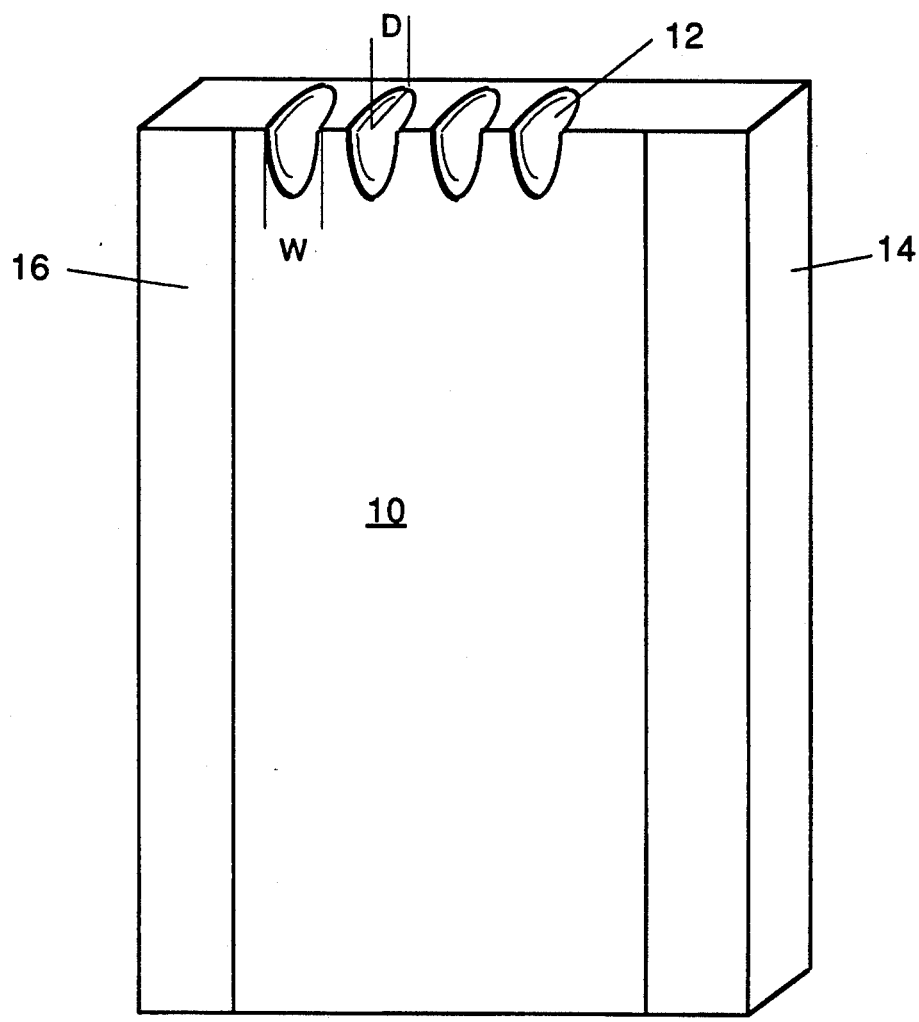
FIG. 1 is a front view of an electrophoresis plate useful in the present invention.
Figure 2:
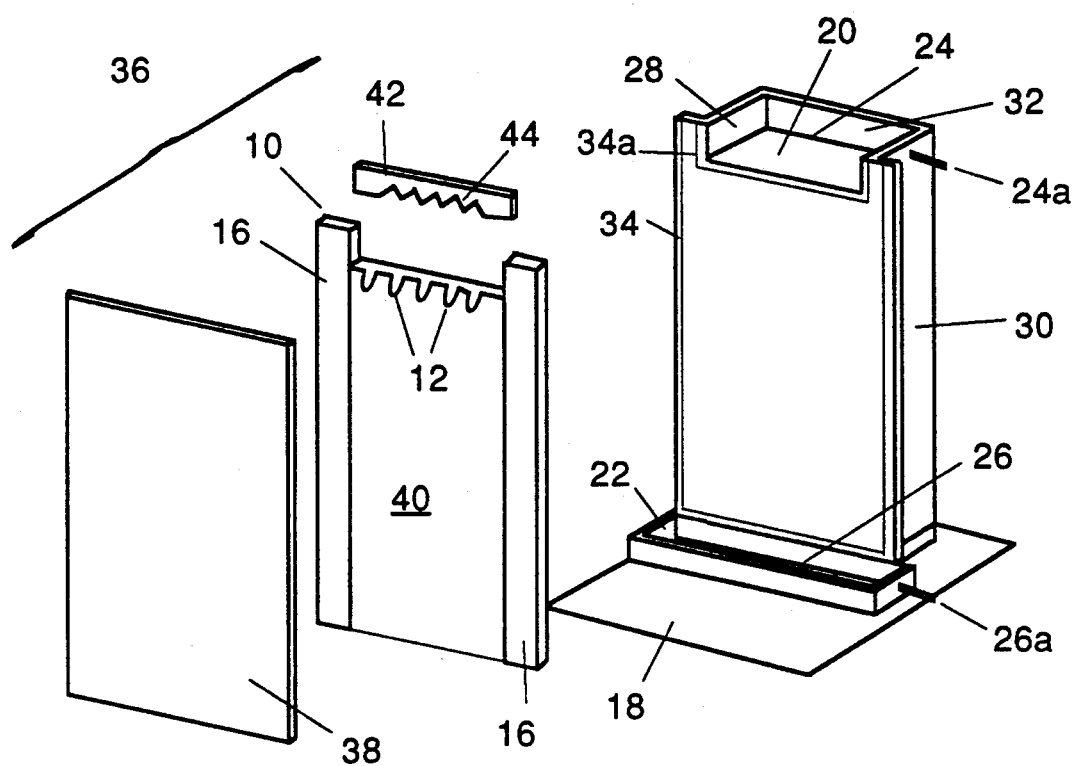
FIG. 2 is an exploded perspective view of an electrophoresis apparatus useful in the present invention.

FIGS. 1 and 2 depict the structure of one embodiment of the present invention. FIG. 1 is a diagram of a plate for an electrophoresis apparatus. The entire apparatus, with the plate of FIG. 1 attached, is illustrated at FIG. 2.

Referring to FIG. 1, a plate 10 contains grooves 12 at the sample-loading end 14 of the plate 10. Plate 10 is typically formed of glass. The grooves 12 are preferably ground into the inside upper edge of plate 10 using a Dremel Moto-Tool (Dremel, Racine, Wisc.) and an oval shaped silicon carbide grinding stone (#84922). Preferably the grooves 12 are conical in shape, vertically extending with a downward taper, although other geometries are suitable. The grooves should be sized and arranged to correspond to the size of the sample wells and the size of the loading pipette tip. A conical shape is preferable because the sample will then collect at the small end of the groove before moving into the gel.

Spacers 16, typically formed of non-conductive material capable of forming a water-tight seal such as polyester or mylar, are placed against the front sides of plate 10. FIG. 2 depicts the arrangement of plate 10 in a typical vertical electrophoresis apparatus. Many other versions of this apparatus exist.

Referring to FIG. 2, the apparatus is composed of a supporting base 18, an upper buffer solution vessel 20 and a lower buffer solution vessel 22 which are mounted on the supporting base 18. An upper electrode 24 and a lower electrode 26, each typically formed of a single platinum wire extending the width of the apparatus, are respectively disposed in the upper buffer solution vessel 20 and the lower buffer solution vessel 22 so that the electrodes 24 and 26 are dipped in a buffer solution when the buffer solution is introduced in the upper buffer solution vessel 20 and the lower buffer solution vessel 22. The electrodes 24 and 26 are respectively connected to external terminals 24a and 26a. Terminals 24a and 26a project outwardly from the sidewalls of the upper buffer solution vessel 20 and the lower buffer solution vessel 22.

The upper buffer solution vessel 20 is defined by side plates 30 and 28, a rear and bottom plate 32 and a front frame 34. A cut-away portion 34a is formed at the upper section of the front frame 34.

Still referring to FIG. 2, an electrophoresis sheet assembly 36 is composed of two flat vertical plates 10 and 38. The vertical plate 38 is the front plate while the vertical plate 10 is the back plate. The two plates are assembled with a spacer 16 between them. The plates are pressed together with the spacer in between. Thus the spacer 16 defines the distance between the plates. The plates 10 and 38 and the spacer 16 define a gel mold into which the electrophoresis gel can be poured to be polymerized in place. Thus the polymeric gel 40 occupies the space in the gel mold between the plates 10 and 38 and spacers 16.

Ultra-thin gels (those less than 0.2 mm) can be formed in many manners. For example, forming an ultra-thin gel using grooved plate 10 for radioactive DNA sequence analysis may comprise the following steps: Plate 10 is coated with gamma-methacryloxypropyltrimethoxysilane (Sigma, St. Louis, Mo.) before the gel 40 is formed to covalently bind gel 40 to plate 10. Plate 38 is treated with a siliconizing agent (Surfasil, Pierce, Rockford, Ill.) to prevent sticking of gel 40. The plates 38 and 10 are clamped together with spacers 16 and placed horizontally on a support, such as an empty ice bucket. A polyacrylamide gel solution is prepared and poured between plates 38 and 10. A comb 42 is cut from the same material as the spacers 16 and is inserted backwards into the space between plates 38 and 10. The presence of comb 42 prevents oxygen from contacting the polyacrylamide solution and, thus, the gel can polymerize.

The size of the spacers, 16, determines the thickness of the gel. Plate assembly 36 is fitted to the front side of the front frame 34 and clamped to the sides of frame 34. As a result, the electrophoresis sheet assembly 36 closes the cut-away portion 34a in the front surface of the upper buffer solution vessel 20. After buffer has been added to the upper buffer chamber 20 and lower buffer chamber 22, a comb 42 is inserted between plates 38 and 10. The teeth 44 of the comb 42 are then slightly imbedded into gel 40. The spaces that form between the teeth 44 and the top of the gel 40 are aligned with grooves 12 such that the teeth 44 are on either side of the individual grooves 12. These spaces formed between the teeth 44 and gel 40 are to be filled with sample. The grooves 12 allow a sample-loading implement to more easily inject a sample into the spaces between the teeth 44 and the top of the gel 40. After the samples are loaded current is applied to the system through external terminals 24a and 26a. The sample will migrate into the gel.

The grooved vertical electrophoresis plate 10 circumvent the difficulties associated with loading samples into ultra-thin gels. The grooves 12 allow a conventional pipette tip (1 mm thick) to be inserted between plates 38 and 10. Plates 38 and 10 are preferably spaced at least 0.070 mm apart. More generally, plates 38 and 10 are spaced less than 0.2 mm apart. The grooves 12 funnel the sample into the middle portion of the well, where the higher density of the sample loading buffer brings it to the gel interface. This arrangement simplifies loading and, thus, running of ultra-thin gels.

Appropriate electrophoresis times vary with the thickness of gel. A 0.075 mm gel that is 40 cm long by 16 cm wide and composed of 6% polyacrylamide/5% bisacrylamide/8M urea may be run at 40 watts constant power (110–135 volts per cm gel) for 30 minutes for a bromphenol blue marker to travel the length of the gel.

Typically, 200 nucleotides can be resolved in a single loading.

At the end of the electrophoretic run, plate 38 is pried away from plate 10. The gel 40 which was covalently bound to plate 10 is fixed with a 10% acetic acid/10% methanol solution for 2 minutes and rinsed thoroughly with water. The gel is dried in less than 15 minutes by placing the MTV plate on an aluminum surface heated to about 70° C. with a laboratory hot plate. Since gel 40 remains attached to the plate 10, it is not damaged by handling. Autoradiography is performed at room temperature.

Most commercially available sequencing apparatus can be adapted to use the plate of FIG. 1. Moreover, the use of this improvement readily permits use of conventional pipettes both to load samples in thin gels (less than 1 mm) and in ultra-thin gels (less than 0.2 mm). The grooves which are used to help define the sample loading wells can be formed in either or both of the vertical plates of the apparatus and can readily be retrofit into existing equipment.

The present invention is not limited to the particular arrangement and construction of parts illustrated herein, but embraces all such modified forms thereof as come within the scope of the following claims.

I claim:

1. An apparatus for conducting electrophoresis comprising
   a base supporting the apparatus;
   a back vertical plate extending upward from the base;
   a front vertical plate extending upward from the base;
   a spacer located between the front vertical plate and the back vertical plate and in contact with each of them so that the spacer defines the distance between the plates, the spacer and the plates defining a gel mold therebetween which is less than 0.2 mm in size;
   means for passing an electric current through a polymerized gel formed in the gel mold;
   one of the vertical plates having formed in it a plurality of vertically extending grooves; and
   a comb corresponding in thickness to the spacer, the comb having teeth formed in its with spaces in between the teeth, the teeth and the grooves on the plate arranged, sized, shaped and located so as to permit samples of biological materials to be loaded into the spaces on the comb aligned with the grooves on the plate for introduction into a gel formed in the gel mold.

2. The apparatus of claim 1 wherein said grooves are conical.

3. The apparatus of claim 1 wherein said means to pass an electrical current includes two buffer reservoirs.

* * * * *